(12) United States Patent
Pohl et al.

(10) Patent No.: US 6,559,329 B2
(45) Date of Patent: May 6, 2003

(54) BLOCKED PHENOLIC SILANES

(75) Inventors: Eric R. Pohl, Mt. Kisco, NY (US); Scot M Turner, Newport, OH (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/981,563

(22) Filed: Oct. 17, 2001

(65) Prior Publication Data

US 2002/0051890 A1 May 2, 2002

Related U.S. Application Data

(62) Division of application No. 09/363,210, filed on Jul. 29, 1999, now Pat. No. 6,413,646.

(51) Int. Cl.$^7$ .................................................. C07F 7/02
(52) U.S. Cl. ....................... 556/437; 556/130; 556/441; 556/446; 556/479
(58) Field of Search ................................ 556/130, 437, 556/446, 441, 479

(56) References Cited

U.S. PATENT DOCUMENTS 5,138,012 A * 8/1992 Riding et al. ............... 525/478

FOREIGN PATENT DOCUMENTS

WO    WO-01090017 A1 * 11/2001

OTHER PUBLICATIONS

Sergeev et al., "Hydrosilylation of Alkenylphenol Acetates with Dichloromethylsilane", Zhurnal Obshchei Khimii, (1982) vol. 52, issue 8, pp. 1846–1849.*

* cited by examiner

*Primary Examiner*—Margaret G. Moore
*Assistant Examiner*—Marc S Zimmer
(74) *Attorney, Agent, or Firm*—Michael P. Dilworth

(57) ABSTRACT

The present invention is directed to a process comprising deblocking a silane of the formula

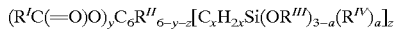

where $R^I$ is H, $CH_3$ or $R^VO$; $R^{II}$ is H or $R^VO$; $R^{III}$ is alkyl, phenyl or acyl from 1 to 6 carbon atoms; $R^{IV}$ is hydrogen, alkyl or phenyl from 1 to 6 carbon atoms; $R^V$ is a linear or branched alkyl group from 1 to 4 carbon atoms; y is an integer from 1 to 3; z is an integer from 1 to 3; x is an integer from 2 to 6 and a is an integer from 0 to 2 to yield a phenolic silane. Also disclosed are processes for making a blocked silane having the above formula.

21 Claims, No Drawings

BLOCKED PHENOLIC SILANES

This application is a Division of application Ser. No. 09/363,210, filed Jul. 29, 1999 now, U.S. Pat. No. 6,413,646.

BACKGROUND OF THE INVENTION

The structures of phenolic silanes are well known in the literature and are disclosed in U.S. Pat. No. 3,328,450. The utility of these phenolic silanes as coupling agents for polyester laminates were discussed in E. P. Plueddemann, H. A. Clark, L. E. Nelson and K. R. Hoffman, *The Society of Plastics Industry, Inc., 17th Annual Meeting of the Reinforced Plastics Divison*, Febuary 6–8, Section 14-A, 1 (1962). 3-(4-Hydroxy-3-methoxyphenyl)propyltrimethoxysilane was found to have excellent force transmission properties for glass fiber reinforced epoxy resins under evaluated temperatures or after exposure to boiling water by A. T. DeBenedetto, J. A. Gomez, C. L. Schilling, F. D. Osterholtz and G. Haddad, *Materials Research Society Symposium Proceeding*, 170, 297 (1990).

A characteristic of these phenolic silanes is that they are unstable. The phenolic hydroxyl group undergoes a transesterification reaction with the alkoxysilyl or acyloxysilyl group to yield oligomers and polymers with high viscosity that may gel. In addition, the oligomers and polymers are very difficult to disperse in water because they are hydrophobic and are not water soluble. An essential end-use requirement is that the phenolic silanes need to be dispersible in water or in aqueous organic solvents, such as mixtures of water with alcohols, ketones, esters or ethers.

The influence of silane spacer groups on the hydrolytic stability of silica reinforced poly-(2,2-bis-[4-(methacryloxy)-2-(hydroxypropyl)phenyl]propane was investigated by N. Nishiyama, K. Horie and T. Asakura, from: *Interfaces in Polymer, Ceramic, and Metal Matrix Composites*, H. Ishida ed., Elsevier Science Publishing Co. Inc., 279 (1988). One silane studied was 4-methacryloyloxy-3-methoxy-1-(3-trimethoxysilylpropyl)benzene. R. H. Chung and W. D. Kray disclosed a series of silylated benzoate esters as an intermediate in making ultraviolet screening agents in U.S. Pat. Nos. 4,328,346 and 4,372,835. For example, they synthesized 2-methoxy-4-(3-methyldimethoxysilylpropyl)phenyl benzoate. When this silane was irradiated with ultraviolet light, it rearranged to make 2-methoxy-4-(3-methyldimethoxysilylpropyl)-6-benzoylphenol. These ester silanes are not suitable for use as coupling agents or as additives to waterborne coatings or primers because the by-products of hydrolysis, benzoic acid or methacrylic acid, are nonvolatile. The nonvolatility of these by-products prevents them from evaporating during the drying or curing process and they remain in the composite or dried coating.

The effects of hydroxyacetophenone structure on the ruthenium catalyzed alkylation using vinylsilanes was investigated by P. W. R. Harris and P. D. Woodgate, *Journal of Organometallic Chemistry*, 530, 211 (1997). Two products that they made were 4-acetoxy-2-(3-triethoxysilylpropyl)acetophenone and 4-acetoxy-2,6-bis-(3-triethoxysilylpropyl)acetophenone. The acetophenone structural fragment may be undesirable because it decomposes when exposed to ultraviolet light. In addition, the acetophenone may react with other ingredients in the composite or coating.

2-(4-Acetoxyphenyl)-1-methyldiclorosilylpropane and 3-(4-acetoxyphenyl)propylmethyldichlorosilane were synthesized as intermediates in the preparation of a phenolic functional silicone fluids, as disclosed in V. A. Sergeev, V. K. Shitikov, G. U. Abbasov, M. R. Bairamov, A. A. Zhdanov, T. V. Astapova and S. M. *Aliev, Zhurnal Obshchel Khimii*, 52, 1846 (1982). The acetyl groups were removed in the base-catalyzed hydrolysis and condensation of the chlorosilane intermediate. Chlorosilanes are not suitable for use in waterborne coatings because they are very corrosive and react very rapidly with water to generate hydrogen chloride.

Other blocking groups have been used to prevent the transesterification reaction of the phenolic hydroxyls with the alkoxysilyl groups. Several trimethylsilyl blocked phenolic chlorosilanes, such as [1-[4-[(trimethylsilyl)oxy]-3-methoxyphenyl]propyl]methyldichlorosilane, were prepared as intermediates in the synthesis of polysilanes, as disclosed by R. Horiguchi, Y. Onishi and S. Hayase, *Macromolecules*, 21, 304 (1988). The trimethylsilyl group was removed by treatment of the polysilane with methanol. However, trimethyl silyl groups are unsuitable for composites, filler treatments and waterborne coating applications. When the blocked silane is added to water, the trimethyl silyl group forms trimethylsilanol, a silylating agent that will react with the inorganic surfaces. The silylation of the surface with trimethyl silyl groups would inhibit the chemical bonding of the silane coupling agent and reduce its efficacy. In addition, the trimethylsilanol can condense with itself to form hexamethyldisiloxane, a water insoluble oily material. Oily materials in the waterborne coating formulations result in poor coating uniformity and often form "fish-eyes" on the surface of applicators or coated substrates.

SUMMARY

The present acyl and carbonate blocked phenolic silanes are latent phenolic functional silanes that are useful as coupling agents for mineral filled composites, surface modifiers for inorganic materials and additives for coatings. These silanes can be used to treat particulate or fibrous inorganic fillers, prime inorganic surfaces, modify the surface properties of inorganic surfaces or modify end-use properties of coatings.

The general structural formula of these silanes is:

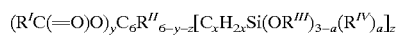

where $R^I$ is H, $CH_3$ or $R^VO$; $R^{II}$ is H or $R^VO$; $R^{III}$ is alkyl, aryl, alkaryl or acyl from 1 to 8 carbon atoms; $R^{IV}$ is hydrogen, alkyl, aryl, or alkaryl from 1 to 8 carbon atoms; $R^V$ is a linear or branched alkyl group from 1 to 4 carbon atoms; y is an integer from 1 to 3; z is an integer from 1 to 3; x is an integer from 2 to 6 and a is an integer from 0 to 2.

DETAILED DESCRIPTION OF THE INVENTION

Structure of the Silanes

The general structural formula of the acyl and carbonate blocked phenolic silanes is set forth above. Additionally, the acyl or carbonate blocking group ($R^IC(=O)$—) needs to generate by-products ($R^IC(=O)OH$ or $CO_2$ and $R^VOH$) that evaporate readily. Therefore the by-products should have a boiling point of less than 120° C. and preferably less than 100° C., at atmospheric conditions. This boiling point requirement can be achieve if the by-products form azeotropes with water. For example, 1-butanol is a potential by-product if the blocking group is butyl carbonate. It forms an azeotrope with water that boils at 93° C. The formyl blocking group is preferred because it deblocks more rapidly when the silane is added to water. The formyl group is more hydrophilic and therefore the solubility of the silane in water is increased. The formyl group also hydrolyzes faster in water. For example, the hydrolysis of 4-nitrophenyl formate is 440 times faster than the corresponding 4-nitrophenyl acetate. See E. R. Pohl, D. Wu, D. J. Hupe, *Journal of the American Chemical Society*, 102, 2759 (1980).

Examples of $R^I$ are hydrogen, methyl, ethoxy, butoxy, isopropoxy or propoxy. Preferred $R^I$ are hydrogen or methyl. Examples of $R^{II}$ are hydrogen, methyl or methoxy. Preferred $R^{II}$ are methoxy and hydrogen. The incorporation of $R^{II}$ that are methoxy increase the solubility of the silane in water. The increase in water solubility shortens the time necessary to hydrolyze the alkoxysilyl ester and remove the blocking group. These $R^{II}$ groups are not reactive with the resins during curing process nor do they increase the formation of undesirable color during the drying process and in-use.

Examples of $R^{III}$ are methyl, ethyl, acyl, formyl, propyl, phenyl, or n-butyl. It is preferred that the $R^{III}$ is methyl, formyl or acyl. The hydrolysis of the methoxysilyl, formyloxysilyl or acetoxysilyl groups are faster than the other $R^{III}$ groups. The replacement of the $R^{III}$ groups with hydrogen, the result of the hydrolysis, aids in dissolving the silane in water.

Examples of $R^{IV}$ are methyl and ethyl. "a" is preferably 0 or 1, most preferably 0. Preferably, x is 2 or 3, and most preferably 3. Preferably, y is 1 and z is 1.

Specific silanes are 4-acetoxy-1-(2-trimethoxysilylethyl) benzene, 2-acetoxy-5-(3-trimethoxysilylpropyl)anisole, 2-methoxy-5-(3-trimethoxysilylpropyl)phenyl formate, 4-acetoxy-1-(1-triacetoxysilylpropyl)benzene, methyl (3-triethoxysilylpropyl)phenyl carbonate, 2-acetoxy-4,6-bis-(3-trimethoxysilylpropyl)anisole, 1-acetoxy-2,4,6-tris (3-trimethoxysilylpropyl)benzene, 1,2-dimethoxy-6-acetoxy-4-(3-triethoxysilylpropyl)benzene, 4-[3-(methyldiethoxysilyl)propyl]phenyl formate, and 4-[3-dimethylmethoxysilylpropyl]-2-methoxyphenyl formate.

UTILITY

The blocking group prevents the transesterification reaction of the phenolic hydroxyl with the alkoxysilyl group. These blocked phenolic silanes are stable when the chemical is stored. They do not polymerize to form oligomers and polymers through the formation of aryloxysilyl bonds. Generally, when the phenolic reactivity is desired in a particular utility, the silane should be deblocked.

The acyl or carbonate blocking group can be removed by hydrolysis with water to form a phenolic silane and by-products (carboxylic acid or carbon dioxide and alcohol). The acyl or carbonate blocking group also can be removed by alcoholysis to form a phenolic silane and by-products (ester or dialkylcarbonate). The acyl or carbonate blocking groups can be removed before or after the silane is used in the application. For example, an aqueous solution of the blocked phenolic silane can be prepared in which the acetoxysilyl or alkoxysilyl group is hydrolyzed in water or aqueous organic solvents to form silanols, but the protecting group has not yet been removed.

These reaction conditions are temperature in the range of 2 to 60° C. and preferably 20 to 40° C., pH of the water or aqueous organic solvents, preferably aqueous alcohols, in the range of pH 3 to 6 and short reaction times of about less than 10 hours for acetyl protecting groups and less than 5 minute for the formyl protecting group. Under these conditions, less than 10 percent of the protecting group will have been removed. If the pH of the solution is below pH of 3 or above pH of 6 and the concentration of the acetyl or carbonate blocked silane is above 1 weight percent, the silanols may condense to form siliconates. These siliconates are undesirable because they may become insoluble in water or aqueous organic solvents. After the acyl or carbonate blocked phenolic silane has been used, such as treating an inorganic surface, the protecting group can then be removed. The removal of the protecting group can be achieved by allowing the acyl or carbonate blocked silane to remain in contact with the water or aqueous organic solvent for periods of time longer than 50 hours for acetyl protecting group or 50 minutes for the formyl protecting group. However, the protecting group can be removed more quickly by adjusting the pH of the water or aqueous organic solvent, raising the temperature or using catalysts. Deblocking occurs faster when the solution is made more acidic than pH of 3 or more alkaline than pH of 9.

Acids that are suitable for adjusting the pH are volatile mineral acids, such as hydrochloric acid or volatile carboxylic acids, such as acetic acid or formic acids. Bases that are suitable include volatile amines, preferably teriary amines, such as trimethyl amine, pyridine, triethylamine. Primary amines are not preferred because they may react with the acyl blocked silane to form nonvolatile amides.

Raising the temperature from ambient to from about 60° C. to refluxing solvent (100° C. degrees for water) promotes the deblocking reaction. Catalysts also may be used. These catalysts include metal ions, such as copper (I), cobalt (II), cobalt (III), manganese (II), calcium ion, titanium (IV), tin (II) and tin (IV), chelated complexes of metal ions, such as acetyl acetonate titanate chelate or ethylacetoacetate titanate chelate, or organometallic compounds, such as dimethyl tin sulfide. Removing the carbonate protecting group is more difficult, and requires catalysts, such as a strong base.

The hydrolysis conditions can be chosen so that both the silane hydrolysis and deblocking reactions occur before use. Alcoholysis can be used to remove the protecting group without hydrolyzing the acyloxysilyl or alkoxysilyl group. The alcoholysis can be achieved by reacting the acyl or carbonate blocked phenolic silane with a volatile alcohol, preferable methanol and ethanol, under ambient conditions. However, under these reaction conditions, the deblocking reactions are very slow. Generally, large excesses of alcohol are used. The deblocking reactions can be catalyzed by acids, such as hydrogen chloride, formic acid or acetic acid, bases, such as tertiary amines, lithium alcoholates, sodium alcoholates, potassium alcoholates, titanium alcoholates, zirconium alcoholates, hafnium alcoholates, or aluminum alcoholates and metal hydroxides. The acyl or carbonate deblocking reaction also is facilitated if the by-product of the alcoholysis are removed by distillation or evaporation. The hydrolysis and alcoholysis reactions are discussed in, *The Chemistry of Carboxylic Acids and Esters*, S. Patai, ed., Interscience Publishers, New York (1969).

The by-products that are formed upon deblocking should be volatile at ambient conditions. They should not adhere to the surface. During the drying and curing processes, these by-products evaporate or distill away from the phenolic silane and therefore will not affect the end-use properties.

The acyl and carbonate blocked phenolic silanes and the phenolic silane that is formed after the blocking group is removed are useful in many applications, especially those where high temperature performance is required. These silanes (blocked and unblocked) are capable of bonding to inorganic substrates. These silanes (blocked and unblocked)

can be used to treat fillers that are used to make composites, such as phenolic break shoe linings. Potential fillers are silicas, titanium dioxide, clays, wollastanite, sand, alumina, aluminosilicates, and glass spheres. The filler may be treated with the blocked silane and be storage stable. When use is desired, the conditions should be such that the blocking group comes off.

Coatings containing these silanes have improved adhesion for applications where adherence to glass, metal or metal oxide is required, such as coil coatings. The deblocked silanes are useful for crosslinking coating and adhesives that contain hydroxyl reactive groups, such as epoxides or isocyanates or which contain alkoxy silane functional groups.

The blocked silanes can be used neat or as an emulsion.

Synthesis of Acyl or Carbonate Blocked Phenolic Silanes

The synthesis of the silanes can be achieve by several different approaches. One approach is to acylate a phenol that contains an alkenyl group followed by the hydrosilation with an alkoxysilane or a chlorosilane. The chlorosilane is reacted further with an alcohol, acid or anhydride. The acylation can be achieved by using acid chlorides, esters or anhydrides. Suitable acylation agents include acetic anhydride, formic and acetic anhydride, acetyl chloride, and methyl formate. Carbonate blocked phenolic silanes are made by reacting the phenol with alkyl chloroformates, dialkyl carbonates or dialkyl pyrocarbonates. Suitable reagents include methyl chloroformate, dimethyl carbonate or diethyl pyrocarbonate. The formylation of the phenolic intermediate can be done by using the procedures described by W. Stevens and A. van Es, *Recueil des Travaux Chimiques des Pays-Bas*, 83, 1287,1294 (1964). The acetylation of the phenolic intermediate can be done by following the procedure described by Ward and Jenkins, *Journal of Organic Chemistry*, 10, 371 (1945). The formation of the carbonates from the phenolic intermediate can be done by procedures referenced in H. J. Schnell, *Chemistry and Physics of Polycarbonates*, Interscience Publishers, New York (1964). The hydrosilation of the resulting product is done by procedures well known in the art and discussed in *Comprehensive Handbook on Hydrosilylation*, B. Marciniec, ed., Pergamon Press, Oxford (1992).

The acyl or carbonate blocked phenolic silanes that have two or three silyl groups can be prepared from dialkenyl or trialkenyl phenol. Representative examples of starting phenols include 2,4-divinylphenol, 2,4,9-trivinylphenol, 2,4-bis-(3-propenyl)phenol, 2,4,6-tris-(3-propenyl)phenol, and 2-methoxy-4,6-bis-(3-propenyl)phenol. The phenolic group is blocked with the acyl or carbonate groups by the procedures discussed above. The alkenyl groups are then hydrosilated with equivalent amount of the chlorosilane or alkoxysilane, as discussed by B. Marciniec, (1992). The chlorosilane are converted to the alkoxysilane or acyloxysilanes by reactions with alcohols, acids or anhydrides, as described by C. Eaborn, *Organosilicon Compounds*, Butterworths Scientific Publications, London (1960).

All of these references to synthetic methods are incorporated herein by reference.

EXAMPLES

Example 1

Synthesis of 2-acetoxy-5-(3-trimethoxysilylpropyl) anisole

Into a three-neck, 5000 ml round bottom flask equipped with an addition funnel, mechanical stirrer, condenser, thermometer, heating mantle and nitrogen inserting tube is charged eugenol (2,519 grams, 15.3 moles). The eugenol was heated to 75° C. The acetic anhydride (1554 grams, 15.2 moles) was added with stirring over a one-hour period. The reaction mixture was then heated to 140° C. and stirred for 3 hours. The acetic acid by-product from the acylation reaction was stripped from the reaction mixture at 36° C. and 0.15 mm Hg pressure. The reaction produced 3-(4-acetoxy-3-methoxyphenyl)propene (3134 grams, 99.3 percent yield.)

In the same reactor vessel, the 3-(4-acetoxy-3-methoxyphenyl)propene was heated to 80° C. and then charged with chloroplatinic acid (0.79 grams). Trimethoxysilane (1990 grams, 16.3 moles) was added with stirring to the reaction mixture over a period of 40 minutes. An ice bath was used to maintain the reaction mixture at a temperature of between 100 and 108° C. After the addition of the trimethoxysilane, the reaction mixture was held at 90° C. for 1 hour and then the mixture was cooled to room temperature. The product was distilled under vacuum at 143° C. and 1 mm Hg.

Stability of the Blocked Phenolic Silane

Comparative Example I

This instability of phenolic silanes was demonstrated by preparing a dilute methanolic solution of 3-(4-trimethylsilyloxy-3-methoxyphenyl) propyltrimethoxysilane. The composition of the solution was 3.58 grams of silane and 3.20 grams of methanol. Decane was used as an internal GC standard. The GC measurements were run on a Hewlett Packard HP 5890A Gas Chromatograph. The column was Hewlett Packard DB-5 with a helium flow rate of 16 ml/minute, initial temperature was 50° C., program rate was 10° C./minute and final temperature was 295° C. The retention time of the 3-(4-trimethylsilyloxy-3-methoxyphenyl) propyltrimethoxysilane was 20.68 minutes. It took less than three days to remove the trimethylsilyl blocking group. The resulting phenolic silane, 2-methoxy-4-(3-trimethoxysilylpropyl)phenol, had a retention time of 19.65 minutes. The disappearance of the phenolic silane (peak at 19.65 minutes) was monitored over a 115 day period. The data, given in Table I, were normalized to 100 percent using the internal decane standard.

TABLE I

The stability of 2-methoxy-4-(3-trimethoxysilylpropyl)phenol in a methanol solvent (47.2 percent methanol) at room temperature.

| Time (days) | Amount of phenolic silane, percent of initial |
| --- | --- |
| 3 | 100 |
| 7 | 102 |
| 86 | 29 |
| 115 | 19 |

These data indicate that the phenolic silane disappears (oligomerizes) even in the presence of methanol, which should retard the transesterification reaction.

Example 2

Stability of 2-acetoxy-5-(3-trimethoxysilylpropyl) anisole

The stability of the blocked phenolic silane was determined by measuring the percent purity of the silane. These measurements were taken immediately after the silane was made and after storing it in a capped glass bottle for 640 days at room temperature. The purity was determined by GC analysis. The instrument was a Hewlett Packard 5890 Series II, equipped with a Hewlett Packard DB-5 capillary column. The GC conditions were initial temperature of 80° C., a two-minute hold, a ramp rate of 10° C. per/minute and a final temperature of 300° C. The retention time of the silane was 16.7 minutes. The purities of the silane after day 1 and day 640 were 96.21 and 96.19 percent, respectively.

Example 3

Aqueous Solutions of 2-acetoxy-5-(3-trimethoxysilylpropyl)anisole

The silane was hydrolyzed by preparing a mixture of 1.5 grams methanol, 0.5 gram silane, 0.25 gram acid or base and 0.5 gram water and stirring for 0.25 hours. This mixture then was added to distilled water to form the noted weight percent solution. Several different hydrolysis conditions were evaluated. The time necessary to form a homogeneous solution of the silane, the stability of the hydrolyzate and the hydrolysis conditions are reported in Table II.

TABLE II

Hydrolysis conditions used to form homogeneous solutions of 2-acetoxy-5-(3-trimethoxysilylpropyl)anisole and stability of the hydrolyzate.

| Example No. | Conc. of silane, % | acid or base | pH | hydrolysis time, hr. | stability of hydrolyzate, hr. |
|---|---|---|---|---|---|
| 3 | 0.5 | Acetic | — | 0.25 | >24 |
| 4 | 0.5 | Acetic | 3.0 | >8 | >24 |
| 5 | 0.5 | Formic | 2.0 | 1.5 | 2.5 |
| 6 | 2.0 | Formic | 2.0 | never formed clear solution | 1.5 |
| 7 | 0.5 | $NH_3$ | 11 | never formed clear solution | <1.0 |

Comparative Example II

Glass Bead Reinforced Phenolic Composite Containing No Silane

A treating solution for glass beads was prepared by mixing 6 grams methanol, 1 gram acetic acid and 97 grams water. The treating solution and 1000 grams of class 4A microbeads that was purchased from Cataphote, Inc. were charged into a 2 liter bottle. The bottle was sealed and then placed on a jar mill for 45 minutes. After mixing, the glass beads were placed into a 20 cm×30 cm steel tray, dried in an oven for 2 hours at 125° C. and then cooled to room temperature.

The treated glass beads (500 grams) were placed into a 4 liter Hobart mixer. Slowly, 54.3 grams of GP 2818 resin that was obtained from Georgia Pacific was added with stirring to the glass beads and mixed for 10 minutes. The small portion of the mixture was then places into a dog-bone mold and compacted using a large rubber stopper. The mold was pretreated with MS 143 TFE release agent that was purchased from Miller Stephenson Chemical Company. The excess mixture was scraped from the mold surface using a metal blade. The molds were placed into a hot air Blue M oven for 1 hour at 200° C. to cure the resin. Twelve dog-bone samples were made. Six of the dog-bone samples was placed into a grip and broken using an Instron 1123 Instrument to determine their dry strengths. Six of the dog-bone samples were place into 50° C. water for 16 hours before determining their wet tensile strength. The average dry and wet tensile strengths are reported in Table III.

Example 4

Glass Bead Reinforced Phenolic Composite Containing 2-acetoxy-5-(3-trimethoxysilylpropyl) anisole 2-Acetoxy-5-(3-trimethoxysilylpropyl)anisole was hydrolyzed by mixing the 2 grams of the silane, 6 grams methanol, 1 gram acetic acid and 2 grams water and stirring for 0.5 hours. The silane hydrolyzate solution was then diluted with 89 grams water.

The 2-acetoxy-5-(3-trimethoxysilylpropyl)anisole hydrolyzate was used to treat the glass beads and to make phenolic composites by the procedure described in Comparative Example II. The tensile strength are reported in Table III. The data indicate that the wet tensile strength of composited made with 2-acetoxy-5-(3-trimethoxysilylpropyl)anisole is 790 percent higher than the control (Comparative Example II).

TABLE III

Tensile strengths of glass bead reinforced phenolic composites.

| Silane | Dry tensile strength, MPa (psi) | Wet tensile strength, MPa (psi) |
|---|---|---|
| None | 2.10 (305) | 0.075 (11) |
| 2-acetoxy-5-(3-trimethoxy-silylpropyl)anisole | 1.54 (224) | 0.60 (87) |

What is claimed is:

1. A process comprising deblocking a silane of the formula $$(R^{I}C(=O)O)_y C_6 R^{II}_{6-y-z}[C_x H_{2x} Si(OR^{III})_{3-a}(R^{IV})_a]_z$$

where $R^I$ is H, $CH_3$ or $R^V O$; $R^{II}$ is H or $R^V O$; $R^{III}$ is alkyl, phenyl or acyl from 1 to 6 carbon atoms; $R^{IV}$ is hydrogen, alkyl or phenyl from 1 to 6 carbon atoms; $R^V$ is a linear or branched alkyl group from 1 to 4 carbon atoms; y is an integer from 1 to 3; z is an integer from 1 to 3; x is an integer from 2 to 6 and a is an integer from 0 to 2 to yield a phenolic silane.

2. The process of claim 1 wherein the deblocking is done by hydrolysis.

3. The process of claim 1 wherein the deblocking is done by alcoholysis.

4. The process of claim 1 wherein a catalyst is present.

5. The process of claim 1 wherein an acid is present and the pH is less than 3.

6. The process of claim 1 wherein the temperature is between about 60 and 100° C.

7. The process of claim 1 wherein $R^I$ is methyl.

8. The process of claim 1 wherein $R^I$ is $R^V O$.

9. The process of claim 1 wherein $R^I$ is selected from the group consisting of ethoxy, butoxy, isopropoxy and propoxy.

10. The process of claim 1 wherein $R^{III}$ is selected from the group consisting of methyl, formyl and acyl.

11. The process of claim 10 wherein a is 0, x=3, y=1 and z=1.

12. The process of claim 1 wherein the silane is selected from the group consisting of: 4-acetoxy-1-(2- trimethoxysilylethyl)benzene, 2-acetoxy-5-(3-trimethoxysilylpropyl)anisole, 2-methoxy-5-(3-trimethoxysilylpropyl)phenyl formate, 4-acetoxy-1-(1-triacetoxysilylpropyl)benzene, methyl (3-triethoxysilylpropyl)phenyl carbonate, 2-acetoxy-4,6-bis-(3-trimethoxysilylpropyl)anisole, 1-acetoxy-2,4,6-tris (3-trimethoxysilylpropyl)benzene, 1,2-dimethoxy-6-acetoxy-4-(3-triethoxysilylpropyl)benzene, 4-[3-(methyldiethoxysilyl)propyl]phenyl formate, and 4-[3-dimethylmethoxysilylpropyl]-2-methoxyphenyl formate.

13. The process of claim 1 wherein the silane is bound to an inorganic substrate.

14. The process of claim 1 wherein the silane is emulsified.

15. A process of manufacturing a silane of the formula

where $R^I$ is H, CH$_3$, or $R^V$O; $R^{II}$ is H or $R^V$O; $R^{III}$ is alkyl, phenyl, or acyl from 1 to 6 carbon atoms; $R^{IV}$ is hydrogen, alkyl, or phenyl from 1 to 6 carbon atoms; $R^V$ is a linear or branched alkyl group from 1 to 4 carbon atoms; y is an integer from 1 to 3; z is an integer from 1 to 3; x is an integer from 2 to 6; and a is an integer from 0 to 2, comprising:

(a) Acylating a phenol of the formula having an alkenyl group to form a phenolic intermediate;

(b) Hydrosilylating the phenolic intermediate onto an alkoxysilane.

16. The process of claim 15 wherein the acylation is conducted with an acid chloride, ester or anhydride.

17. The process of claim 16 wherein the phenolic intermediate is hydrosilated onto an alkoxysilane.

18. The process of claim 15 wherein the silane produced has the formula:

where $R^I$ is H, CH$_3$ or $R^V$O; $R^{II}$ is H or $R^V$O; $R^{III}$ is alkyl, phenyl or acyl from 1 to 6 carbon atoms; $R^{IV}$ is hydrogen, alkyl or phenyl from 1 to 6 carbon atoms; $R^V$ is a linear or branched alkyl group from 1 to 4 carbon atoms; y is an integer from 1 to 3; z is an integer from 1 to 3; x is an integer from 2 to 6 and a is an integer from 0 to 2.

19. A process according to claim 15 wherein the phenolic intermediate is a dialkylkenyl or trialkenyl phenol.

20. The process of claim 15 wherein the silane is selected from the group consisting of: 4-acetoxy-1-(2-trimethoxysilylethyl)benzene, 2-acetoxy-5-(3-trimethoxysilylpropyl)anisole, 2-methoxy-5-(3-trimethoxysilylpropyl)phenyl formate, 4-acetoxy-1-(1-triacetoxysilylpropyl)benzene, methyl (3-triethoxysilylpropyl)phenyl carbonate, 2-acetoxy-4,6-bis-(3-trimethoxysilylpropyl)anisole, 1-acetoxy-2,4,6-tris (3-trimethoxysilylpropyl)benzene, 1,2-dimethoxy-6-acetoxy-4-(3-triethoxysilylpropyl)benzene, 4-[3-(methyldiethoxysilyl)propyl]phenyl formate, and 4-[3-dimethylmethoxysilylpropyl]-2-methoxyphenyl formate.

21. A process of manufacturing a silane of the formula

where $R^I$ is H, CH$_3$, or $R^V$O; $R^{II}$ is H or $R^V$O; $R^{III}$ is alkyl, phenyl, or acyl from 1 to 6 carbon atoms; $R^{IV}$ is hydrogen, alkyl, or phenyl from 1 to 6 carbon atoms; $R^V$ is a linear or branched alkyl group from 1 to 4 carbon atoms; y is an integer from 1 to 3; z is an integer from 1 to 3; x is an integer from 2 to 6; and a is an integer from 0 to 2, comprising:

(a) Acylating a phenol of the formula having an alkenyl group to form a phenolic intermediate;

(b) Hydrosilylating the phenolic intermediate onto a chlorosilane; and (c) Further reacting the product obtained in step (b) with an alcohol, acid, or anhydride.

* * * * *